US009983393B2

(12) United States Patent
Esteban Finck et al.

(10) Patent No.: US 9,983,393 B2
(45) Date of Patent: May 29, 2018

(54) CATOPTRIC IMAGING DEVICE FOR DRILL MEASURING

(71) Applicant: AIRBUS DEFENCE AND SPACE, S.A., Getafe (Madrid) (ES)

(72) Inventors: Fernando Enrique Esteban Finck, Getafe (Madrid) (ES); David Gomez Esteban, Getafe (Madrid) (ES); Francisco José León Arevalo, Getafe (Madrid) (ES); Luis Granero Montagud, Burjassot (Valencia) (ES); Martín Sanz Sabater, Burjassot (Valencia) (ES); Vicente Mico Serrano, Burjassot (Valencia) (ES); Javier Garcia Monreal, Burjassot (Valencia) (ES)

(73) Assignee: Airbus Defence and Space, S.A., Madrid (ES)

( * ) Notice: Subject to any disclaimer, the term of this patent is extended or adjusted under 35 U.S.C. 154(b) by 211 days.

(21) Appl. No.: 15/146,474

(22) Filed: May 4, 2016

(65) Prior Publication Data
US 2016/0327775 A1 Nov. 10, 2016

(30) Foreign Application Priority Data
May 7, 2015 (EP) .................................... 15382237

(51) Int. Cl.
*G02B 17/02* (2006.01)
*H04N 5/369* (2011.01)
(Continued)

(52) U.S. Cl.
CPC ............ *G02B 17/026* (2013.01); *G01B 11/12* (2013.01); *G01B 11/24* (2013.01); *G01M 13/00* (2013.01);
(Continued)

(58) Field of Classification Search
CPC ...... G02B 17/026; G02B 23/24; G02B 5/136; G01B 11/24
See application file for complete search history.

(56) References Cited

U.S. PATENT DOCUMENTS 4,967,092 A * 10/1990 Fraignier ............... G01B 11/24
250/559.07
8,841,603 B1  9/2014 Blanton et al.
(Continued)

FOREIGN PATENT DOCUMENTS

DE           196 18 558 A1   11/1997
DE    10 2004 043209 A1    3/2006

OTHER PUBLICATIONS

Extended European Search Report for Application No. EP 15 38 2237 dated Oct. 13, 2015.

*Primary Examiner* — Nam Pham
(74) *Attorney, Agent, or Firm* — Jenkins, Wilson, Taylor & Hunt, P.A.

(57) ABSTRACT

A catoptric imaging device for drill measuring comprising a laser guide, an imaging unit for converting optical image into image information, and processing the image information to obtain a drill measure, a catoptric assembly including a first conical surface, and a second surface including a frustoconical surface, wherein the first surface is arranged relative to the laser guide to reflect a cone beam onto an cross section of the drill to be measured, and wherein the smallest diameter of the frustoconical surface is larger than the largest diameter of the first surface to receive the cone beam reflections and reflect them towards the imaging unit, and wherein the imaging unit is arranged to receive an optical image from the frustoconical surface reflections to obtain a drill measure.

11 Claims, 4 Drawing Sheets

(51) Int. Cl.
| | |
|---|---|
| *G01M 13/00* | (2006.01) |
| *G01B 11/12* | (2006.01) |
| *G01B 11/24* | (2006.01) |
| *G02B 5/136* | (2006.01) |
| *G02B 23/24* | (2006.01) |
| *G01N 21/954* | (2006.01) |

(52) U.S. Cl.
CPC ............ *G02B 5/136* (2013.01); *G02B 23/24* (2013.01); *H04N 5/369* (2013.01); *G01N 21/954* (2013.01); *G01N 2021/9548* (2013.01)

(56) References Cited

U.S. PATENT DOCUMENTS

| | | |
|---|---|---|
| 9,234,748 B2 | 1/2016 | Bondurant et al. |
| 2014/0368834 A1 | 12/2014 | Bondurant et al. |

\* cited by examiner

CATOPTRIC IMAGING DEVICE FOR DRILL MEASURING

CROSS-REFERENCE TO RELATED APPLICATION

This application claims the benefit of and priority to European patent application No. 15 382237.4 filed on May 7, 2015, the entire disclosure of which is incorporated by reference herein.

TECHNICAL FIELD

The present disclosure refers to a catoptric imaging device that includes optical, imaging, and a processor for performing drill measurements. These allow the device obtaining optical information from the drill to be measured, and, from that, obtaining processable information to finally calculate at least a measure of a drill. The disclosure herein further refers to a catoptric imaging system that comprises the catoptric imaging device.

An object of the disclosure herein is to provide a catoptric imaging device capable of obtaining information of a complete cross section of a drill, by a simplified and compact device that can be introduced into any kind of drill or bore to measure.

Another object of the present disclosure is to provide a catoptric imaging device capable of preventing from the need of contacting the surface to measure for providing a surface measurement.

Another object of the present disclosure is to provide a catoptric imaging system capable of scanning the entire length of the drill along a measuring axis for providing a complete profile characterization of the drill to measure. Additionally, it is also an object of the present disclosure to provide a way for generating an image of the measured drill that is suitable for performing visual inspection.

BACKGROUND

Industries use drills in components for assembling products. Such drills can be of variable size and be performed on a wide variety of materials. The aircraft industry is a prime example of an industry that uses drills of various sizes in a variety of components formed of various metals, such as aluminum, titanium, and synthetic materials, such as composite.

In order to ensure a secure product assembling, drills are inspected to verify that fulfil with the drill current regulations established by the airworthiness directives. The regulations define the geometry characteristics that drills must comply.

Traditionally, drills have been sized by inserting them by hand into bushings that gauge the drill diameter. Like most manual processes, the process lacks of reliability since the gauging depends both on the operator's interpretation and the bushing condition. In addition, manual sizing becomes most difficult when a large number of drills separated by small gaps have to be sized, or when drills are in a product with difficult access.

Further, manual sizing is a slow and expensive task, particularly, when it is necessary to size a large number of drills of variable size, which have been performed over variable materials. The drill behavior varies depending on the material. Thus, in the aircraft industry, the drill sizing has to be particularly performed over aluminum, titanium, and composite, which form the most common materials used in the sector. Moreover, composite involves an added difficult since it should be treated as a family of materials due to the great variety of materials that can be obtained by varying the fiber material, the layout, the stacking, the resin material, or the curing time.

Nowadays, most of these limitations have been reduced by the use of optical technology. This technology has significantly improved the drill measuring accuracy.

One example of this optical technology is the patent application U.S. 2014/0368834 A1. The application describes an optical thread profiler capable of measuring at least one physical characteristic of an internally threaded surface of an object. The apparatus performs laser triangulation measurements. However, the described apparatus requires making physical contact with the object to be measured, which complicates and slows down the measuring task. Also, the apparatus requires performing numerous movements and measures to get one physical characteristic of the drill.

Therefore, it has been detected in the aeronautical industry the need of a new device which be able to reduce the time required for obtaining drill measures, and that achieves simplifying the drill measuring task.

SUMMARY

The present disclosure overcomes the above mentioned drawbacks by providing a catoptric imaging device that simplifies the drill measuring by providing a versatile device capable of measuring different sizes of drills. Besides, the device enables reducing the time required for obtaining a drill measure.

An aspect of the disclosure herein refers to a catoptric imaging device for drill measuring that comprises a laser guide, an imaging unit, and a catoptric assembly. The laser guide is suitable for guiding a laser beam. The imaging unit comprises an imaging element configured to photoelectrically convert an optical image into image information, and an image processor configured to obtain at least one drill measure from the image information. The catoptric assembly comprises a first conical surface, and a second surface arranged below the first surface and comprising a frustoconical surface, wherein both surfaces are coaxially aligned with respect to a measuring axis. The first surface is arranged relative to the laser guide to reflect a cone beam onto an annular cross section of the drill to be measured. The smallest diameter of the frustoconical surface is larger than the largest diameter of the first surface to receive the cone beam reflections and reflect the cone beam reflections towards the imaging unit. The imaging unit is arranged to receive an optical image from the frustoconical surface reflections for generating the drill image information and finally obtaining the at least one drill measure.

Providing a conical configuration to the first surface of the catoptric assembly, and disposing the first conical surface aligned with the laser guide so as to generate a cone beam from the laser beam received from the laser guide, the disclosure herein achieves illuminating an entire cross section of the drill to be measured. This way, the device can measure a complete cross section at once, without the need of moving the device axially. Thus, the disclosure herein reduces the time conventionally required for measuring a drill cross section in a simple, effective, and accuracy manner.

Additionally, the catoptric assembly provides a second surface, arranged below the first surface and coaxially aligned with respect to the measuring axis, to provide a way for capturing the cone beam reflections. These cone beam reflections carry the drill optical information. The second surface comprises a frustoconical surface configured so as to receive the cone beam reflections, and reflect them towards the imaging unit. For that, the smallest diameter of the frustoconical surface is larger than the largest diameter of the first surface.

This way, the catoptric assembly according to the disclosure herein, provides both for illuminating the drill to be measured and for capturing the optical information.

Additionally, the device comprises an imaging unit arranged to receive the frustoconical surface reflections. These reflections form an optical image and carry the drill optical information. The imaging element of the imaging unit photoelectrically converts the optical image (optical information) into processable electric data (image information). The image processor processes the image information for obtaining at least one drill measure.

In addition, disposing the imaging unit aligned with the laser guide, and with the first and second surfaces of the catoptric assembly, the disclosure herein offers a compact device suitable for being introduced in any kind of drill, bore, or hole to measure.

Besides, given that the catoptric imaging device avoids the need of making physical contact for measuring, the device enables to simplify and expedite the measuring task.

Another aspect of the disclosure herein refers to a catoptric imaging system that comprises the catoptric imaging device according to the present disclosure, a laser source for providing a laser beam to the laser guide, and a scanning system adapted to move the catoptric imaging device along the measuring axis. This way, the disclosure herein achieves measuring the drill length by simply moving the catoptric imaging device along the measuring axis. Thus, the system is able to provide a complete profile of the measured drill.

BRIEF DESCRIPTION OF THE DRAWINGS

For a better comprehension of the disclosure herein, the following drawings are provided for illustrative and non-limiting purposes, wherein.

DETAILED DESCRIPTION

Figure 1:
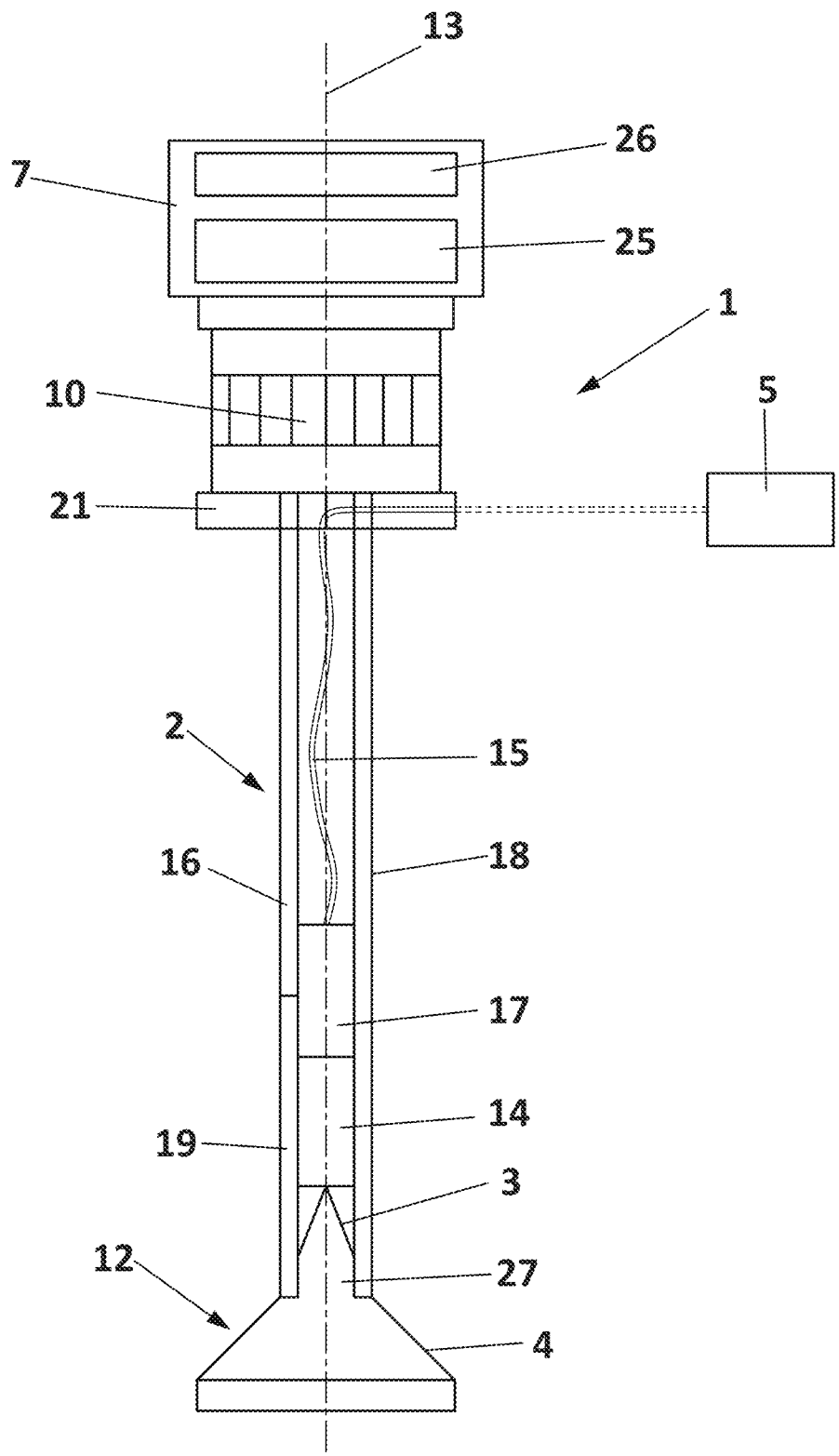
FIG. 1 shows a longitudinal section view of a catoptric imaging device according to an embodiment of the present disclosure.

FIG. 1 shows a catoptric imaging device 1 that comprises a laser guide 2 for guiding a laser beam 24 from a laser source 5, a catoptric assembly 12 arranged below the laser guide 2 for receiving the laser beam 24, and an imaging unit 7 arranged above the laser guide 2 for receiving the optical information provided by a part of the catoptric assembly 12.

As shown, the imaging unit 7, the laser guide 2, and the catoptric assembly 12 are aligned along a common measuring axis 13. The measuring axis 13 matches the catoptric imaging device longitudinal axis.

The catoptric assembly 12 comprises a first conical surface 3 positioned to receive the laser beam 24 guided by the laser guide 2. The catoptric assembly 12 further comprises a second surface comprising a frustoconical surface 4 to receive the drill optical information and reflect it towards the imaging unit 7. Both surfaces 3, 4 are coaxially aligned with respect to the measuring axis 13. The frustoconical surface 4 is arranged below the first surface 3, and is wider than the first conical surface 3, that is, the smallest diameter of the frustoconical surface 4 is larger than the largest diameter of the first surface 3.

The shape of the first surface 3 causes the laser beam 24 conducted by the laser guide 2 to be reflected as a cone beam 9. The cone beam strikes a complete annular cross section of the drill 6 to be measured.

The frustoconical shape allows, in first place, collecting the cone beam reflections 10 onto the drill 6 to be measured, and in second place, reflecting the cone beam reflections upwards toward the imaging unit 7.

The imaging unit 7 comprises an imaging element 25 for photoelectrically converting the optical image received from the frustoconical surface 4 reflections, into image information. The imaging element 25 is a semiconductor element, typically a CCD or a CMOS image sensor, and has an imaging function of receiving light from an object and capturing an image of the object. Further, the imaging unit 7 comprises image processor 26 for processing the image information to obtain at least one drill measure.

According to a preferred embodiment, the image processor 26 is further configured to calculate the diameter of the drill 6 from the drill image information.

According to another preferred embodiment, the image processor 26 is further configured to calculate the cylindricity of the drill 6 from the drill image information. This way, the catoptric imaging device 1 allows measuring the drill tilting.

According to another preferred embodiment, the image processor 26 is further configured to calculate the ovalization of the drill 6 from the drill image information. This way, the disclosure herein allows measuring the drill deformation.

In a preferred embodiment, the laser guide 2 comprises an optical fiber 15 for guiding the laser beam 24 from a laser source 5, and a probe 16 for enclosing the optical fiber 15. The probe longitudinal axis matches the measuring axis 13.

Preferentially, the optical fiber 15 is mounted along to a ferrule 17 whose diameter matches the diameter of the fiber cladding. The optical fiber ferrule 17 holds the optical fiber 15 and helps to align and secure the fiber mechanically.

As shown in FIG. 1, the probe 16 may comprise different sections. Preferentially, the probe 16 comprises a first section 18 made of steel, and a second section 19 made of a translucent material. The translucent material is such that allows a laser beam to pass through it. Preferably, such translucent material will be glass.

According to a preferred embodiment, the catoptric assembly 12 has a single body formed by an upper part comprising a conical section having the conical surface 3, and a lower part having a frustoconical configuration and having the frustoconical surface 4.

In a preferred embodiment, as shown in FIG. 1, the first conical surface 3 is fitted at one end of the probe 16. To improve this fitting, the upper part of the body may comprise a tubular section 27 below the conical section, which is flush with the conical section. Also, this tubular section 27 eases the coupling and uncoupling of the catoptric assembly 12 to the probe 16. Additionally, this tubular section 27 may form a shoulder with the frustoconical surface 4 to receive the end of the probe 16.

At the opposite end, the probe 16 is coupled to the imaging unit 7. The imaging unit 7 may further comprise a plurality of lenses 20 that condense light from outside before reaching the imaging element 25. The plurality of lenses 20 are assembled in a lens holder so that respective centers thereof are positioned on the same axis, the measuring axis 13.

Preferably, as shown in FIG. 1, the lens holder comprises at its base a clamping plate 21 for engaging the probe 16 and supporting the imaging unit 7 outside the drill to inspect.

Figure 2:
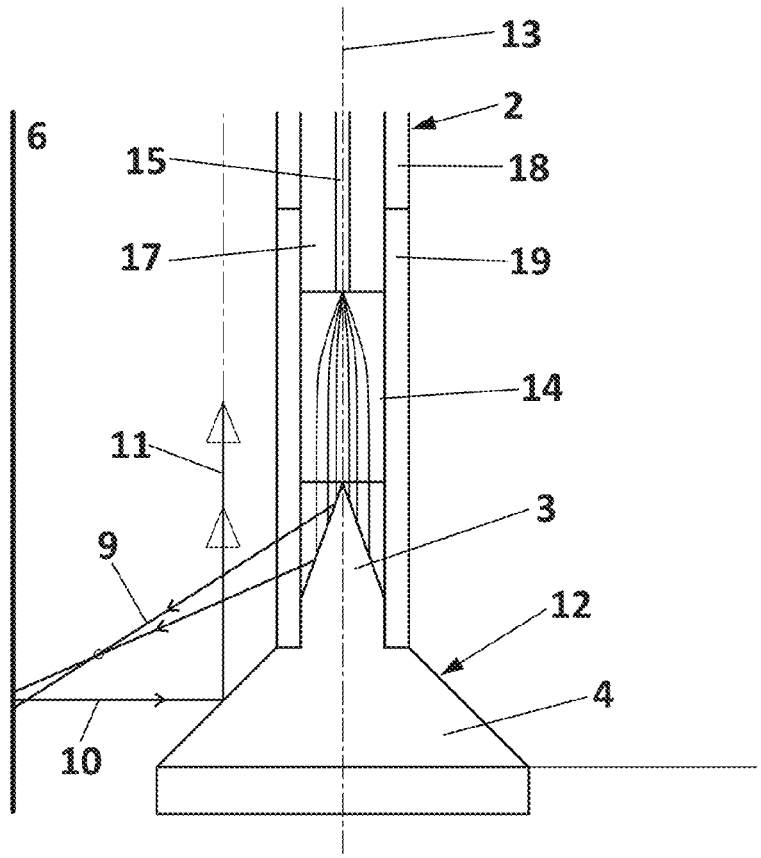
FIG. 2 shows a detailed view of the optical paths followed by the laser beam since the laser beam output the laser guide until the drill optical information is directed towards the imaging unit.

As shown in FIGS. 1 and 2, the laser guide 2 may further comprise a lens 14 placed at the optical fiber 15 output to collimate the laser beam 24 guided by the fiber 15. Preferably, the lens 14 is a GRIN lens, suitable for confined spaces.

FIG. 2 shows the effect of the GRIN lens 14. The lens 14 collimates the laser beam 24 upon exiting the optical fiber 15 to generate a narrow beam. This narrow beam is directed to the vertex of the first conical surface 3 to generate a conical beam 9. The GRIN lens length is selected such that at the exit face of the GRIN lens the beam exhibits a slight convergence, focusing to a distance given by the expected location of the drill wall. Therefore, at that distance the vertical width of the conical beam is minimal.

The conical beam 9 strikes onto a complete cross section of the drill 6 to measure. This way, the device 1 provides information of the entire section without having to rotate the device 1 about the measuring axis 13, or having to contact the drill 6. This results on a simpler and faster measuring task.

The cone beam reflections 10 are received by the frustoconical surface 4, and subsequently reflected towards the imaging unit 7 location. The imaging unit 7 converts drill optical image into drill image information.

Figure 3:
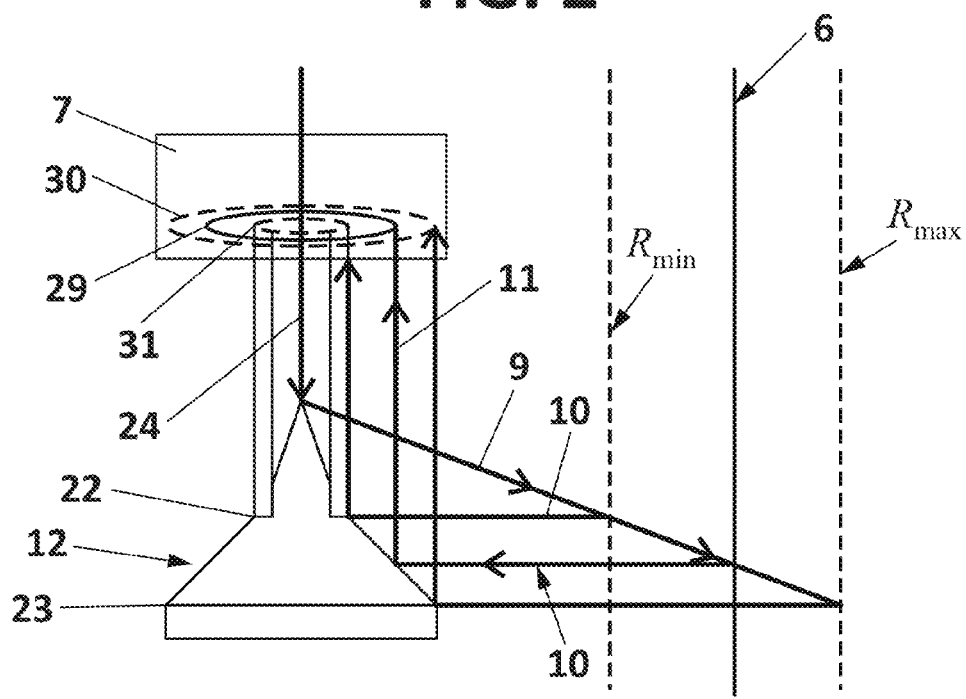
FIG. 3 shows the minimum and maximum measurable radius of a drill when using the catoptric imaging device of the disclosure herein.

FIG. 3 schematically shows the optical paths followed by the laser beam 24 since outputs the optical fiber until taking the imaging unit 7 direction. As shown, the frustoconical surface 4 configuration determines the measurable diameter range. The smallest diameter 22 of the frustoconical surface 4 sets the minimum measurable diameter, whereas the largest diameter 23 sets the maximum measurable diameter.

FIG. 3 also shows in a schematic way the potential images that would be formed from the different frustoconical surface reflections 11. In particular, the images 31, 30 corresponding to the minimum and maximum measurable diameters, and the image 29 corresponding to the diameter of the measured drill 6.

Figure 4:
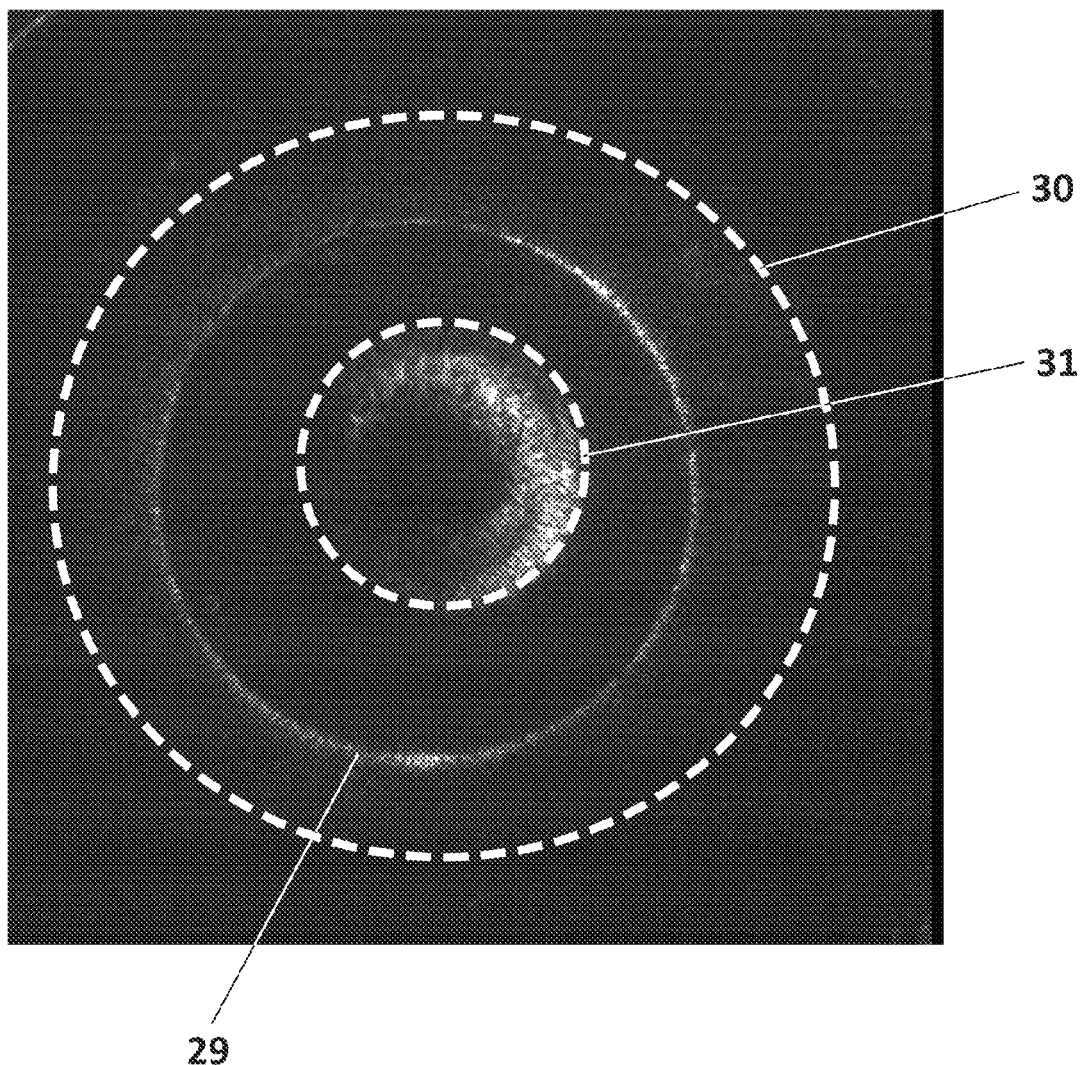
FIG. 4 shows images of drills with different cross sections. In dash lines, the figure represents the minimum and maximum measurable cross sections.

According to a preferred embodiment, the imaging unit 7 further comprises a display configured to display the drill image information. FIG. 4 represents the image that would show the display in the exemplary case of FIG. 3. For illustrative purposes, FIG. 4 additionally shows in dashed lines the images 31, 30 corresponding to the smallest 22 and largest diameter 23 of the frustoconical surface 4, which informs about minimum and maximum measurable diameters. The area between the minimum and maximum measurable diameters determines the measurable area of the device 1.

Figure 5:
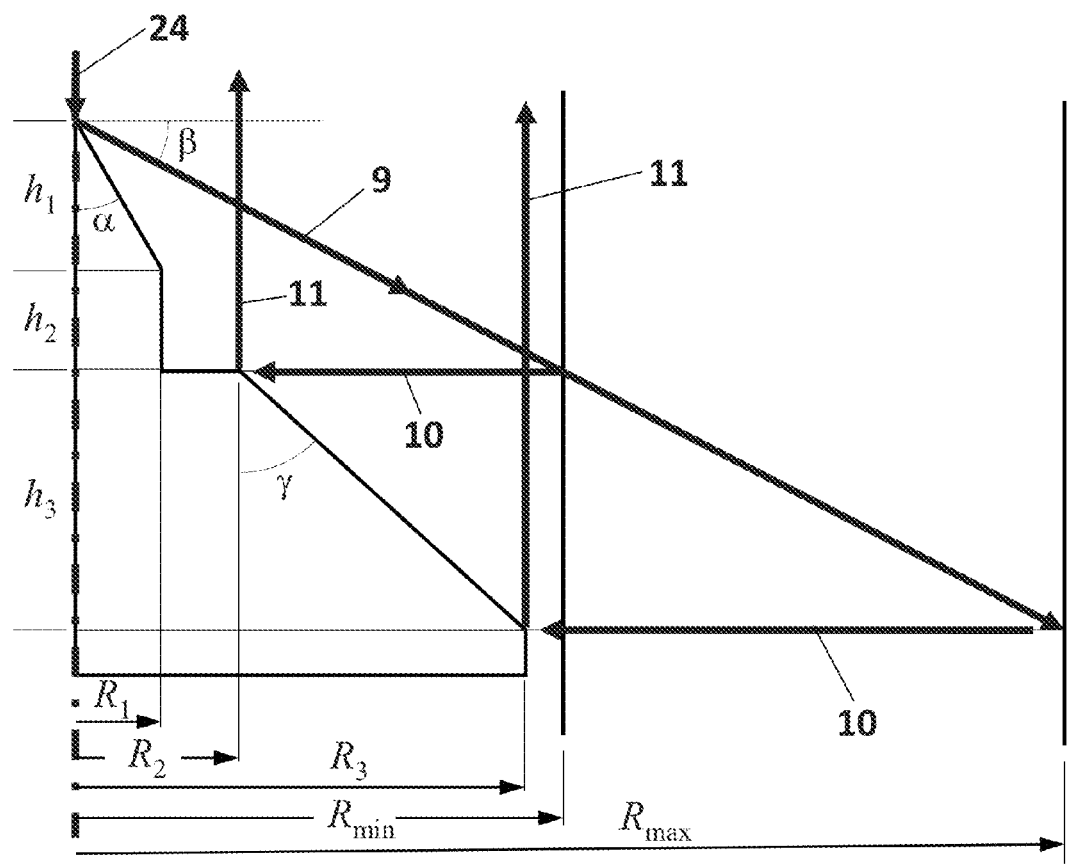
FIG. 5 shows a detailed view of angular and radial parameters defined by the catoptric assembly configuration and the optical paths followed by the laser beam upon exiting the laser guide.

FIG. 5 shows the geometry associated to the catoptric assembly 12 configuration shown in FIGS. 1, 2 and 3, and to the optical paths followed by the laser beam since exiting the laser guide until directed towards the imaging unit 7.

The narrow beam, generated at the GRIN lens 14 output, strikes the apex of the first conical surface 3. The first conical surface 3 forms a half angle $\alpha$ with respect to a vertical plane. Hence, the narrow beam becomes a narrow cone beam 9 with aperture $\beta$ with respect to a horizontal plane. The cone beam 9 strikes onto the drill to be measured, and the light diffused by the drill wall is reflected in the frustoconical surface 4, which forms a half angle $\gamma$ with respect to the vertical plane.

Assuming that the $\gamma$-angle is 45 sexagesimal degrees, the image processor 26 is configured to obtain at least one drill measure considering the following parameters:

$R_{min}$: minimum measurable radius,
$R_{max}$: maximum measurable radius,
$R_1$: first conical surface diameter,
$R_2$: smallest radius of the frustoconical surface,
$R_3$: largest radius of the frustoconical surface (catoptric imaging device radius),
$\alpha$: half angle of the first conical surface,
$\beta$: cone beam angle with respect to a horizontal plane,
$\gamma$: half angle of the frustoconical surface.

With these parameters, the image processor 26 will make use of the following relations to finally obtain at least one drill measure:

$$\tan\beta = \frac{R_3 - R_2}{R_{max} - R_{min}} \quad [1]$$

$$\tan\alpha = \frac{1}{\tan\beta} \quad [2]$$

$$h_1 = \frac{R_1}{\tan\alpha} \quad [3]$$

$$h_2 = R_{min}\tan\beta - h_1 \quad [4]$$

$$h_3 = R_3 - R_2 \quad [5]$$

From the above mentioned relations, the image processor 26 is adapted to calculate the diameter of the measured drill 6, the tilt of the drill, or the drill deformation. Also, the image processor 26 is adapted to detect small defects, such as tool grooves.

Finally, the catoptric imaging device 1 can be used to characterize a complete profile of a drill by just including a laser source to feed the laser guide, and a scanning system for moving the catoptric imaging device along the measuring axis.

While at least one exemplary embodiment of the present invention(s) has been shown and described, it should be understood that modifications, substitutions and alternatives may be apparent to one of ordinary skill in the art and can be made without departing from the scope of the disclosure described herein. This application is intended to cover any adaptations or variations of the specific embodiments discussed herein. In addition, in this disclosure, the terms "comprise" or "comprising" do not exclude other elements or steps, and the terms "a" or "one" do not exclude a plural number. Furthermore, characteristics or steps which have been described with reference to one of the above exemplary embodiments may also be used in combination with other characteristics or steps of other exemplary embodiments described above.

The invention claimed is:

1. A catoptric imaging device for drill measuring comprising:
   a laser guide for guiding a laser beam;

an imaging unit comprising an imaging element configured to photoelectrically convert an optical image into image information, and an image processor configured to obtain at least one drill measure from the image information;

a catoptric assembly comprising a first conical surface, and a second surface arranged below the first conical surface and comprising a frustoconical surface, wherein both surfaces are coaxially aligned with respect to a measuring axis; and wherein the first surface is arranged relative to the laser guide to reflect a cone beam onto an annular cross section of the drill to be measured, wherein a smallest diameter of the frustoconical surface is larger than a largest diameter of the first surface to receive the cone beam reflections and reflect the cone beam reflections towards the imaging unit, wherein the laser guide is disposed between the imaging unit and the catoptric assembly, and wherein the imaging unit is arranged to receive an optical image from the frustoconical surface reflections for generating the drill image information and finally obtaining the at least one drill measure.

2. A catoptric imaging device according to claim 1, wherein the catoptric assembly has a single body formed by an upper part comprising a conical section, and a lower part having a frustoconical configuration.

3. A catoptric imaging device according to claim 2, wherein the upper part further comprises a tubular section below the conical section, and wherein the tubular section is flush with the conical section.

4. A catoptric imaging device according to claim 1, wherein the laser guide comprises an optical fiber for guiding the laser beam, and a probe for enclosing the optical fiber, and wherein the probe longitudinal axis matches the measuring axis.

5. A catoptric imaging device according to claim 4, wherein the first conical surface is fitted at one end of the probe, and wherein the end is made of translucent material for allowing the cone beam to pass.

6. A catoptric imaging device according to claim 4, wherein the laser guide comprises at least one lens at the optical fiber output to collimate the laser beam.

7. A catoptric imaging device according to claim 1, wherein the image processor is configured to calculate diameter of the drill from the drill image information.

8. A catoptric imaging device according to claim 1, wherein the image processor is configured to calculate cylindricity of the drill from the drill image information.

9. A catoptric imaging device according to claim 1, wherein the image processor is configured to calculate ovalization of the drill from the drill image information.

10. A catoptric imaging device according to claim 1, wherein the imaging unit further comprises a display configured to display the drill image information.

11. A catoptric imaging system for drill measuring comprising:
    the catoptric imaging device according to claim 1;
    a laser source for providing a laser beam to the laser guide of the catoptric imaging device; and
    a scanning system adapted to move the catoptric imaging device along the measuring axis.

* * * * *